United States Patent [19]

Anderson et al.

[11] 4,267,359

[45] May 12, 1981

[54] NOVEL CARBOXYLIC ACID ESTERS

[75] Inventors: Richard J. Anderson; Clive A. Henrick, both of Palo Alto, Calif.

[73] Assignee: Zoecon Corporation, Palo Alto, Calif.

[21] Appl. No.: 15,569

[22] Filed: Feb. 26, 1979

Related U.S. Application Data

[62] Division of Ser. No. 902,624, May 4, 1978, Pat. No. 4,204,071.

[51] Int. Cl.$^3$ ............... C07C 69/76; A01N 37/10
[52] U.S. Cl. ............... 560/104; 560/55; 560/100; 424/308
[58] Field of Search ............... 560/104, 55, 100

[56] References Cited

U.S. PATENT DOCUMENTS

| | | | |
|---|---|---|---|
| 3,996,244 | 12/1976 | Fujimoto et al. | 560/104 |
| 4,161,535 | 7/1979 | Meyer et al. | 560/104 |

*Primary Examiner*—Alan Siegel
*Attorney, Agent, or Firm*—Donald W. Erickson

[57] ABSTRACT

Esters and thiolesters of α-substituted unsaturated acids, intermediates therefor, synthesis thereof, and the use of said esters and thiolesters and compositions thereof for the control of pests.

15 Claims, No Drawings

NOVEL CARBOXYLIC ACID ESTERS

This is a division of application Ser. No. 902,624, filed May 4, 1978, now U.S. Pat. No. 4,204,071.

This invention relates to novel esters and thiolesters of α-substituted unsaturated acids, novel intermediates therefor, synthesis thereof, and the control of pests.

The esters and thiolesters of the present invention are represented by the following formula (A):

$$R^1-\underset{R^3}{\underset{|}{C}}=\underset{|}{\overset{R^2}{C}}-\underset{|}{\overset{R^4}{CH}}-\overset{O}{\overset{\|}{C}}-WR^5 \quad (A)$$

wherein,

W is oxygen or sulfur;

$R^1$ is phenyl, substituted phenyl, or naphthyl;

each of $R^2$ and $R^3$ is independently selected from hydrogen, chloro, fluoro, bromo, lower alkyl, lower alkenyl, lower alkoxy, cycloalkalkyl, and lower haloalkyl;

$R^4$ is lower alkyl of 2 to 5 carbon atoms, lower alkenyl of 2 to 5 carbon atoms, or cyano; and $R^5$ is one of the groups $$-CHR^6-\underset{R^9}{\overset{R^7{}_p}{\underset{\phantom{x}}{\bigcirc}}}-R^8 \quad \text{or} \quad -CHR^6-\underset{W}{\overset{R^{10} \; R^{11}}{\bigcirc}}$$

in which, p is zero, one, two, or three;

$R^6$ is hydrogen, cyano, methyl, or ethynyl;

$R^7$ is halogen, lower alkyl, lower haloalkyl, lower alkoxy, lower haloalkoxy, lower alkylthio, lower alkenyl, or lower haloalkenyl;

$R^8$ is hydrogen or together with $R^7$ forms a lower alkylenedioxy bridge across adjacent ring carbon atoms;

$R^9$ is hydrogen, lower alkenyloxy, lower alkynyl, lower alkynyloxy, lower haloalkynyl, lower alkylcarbonyl, arylcarbonyl, substituted arylcarbonyl, aryloxy, substituted aryloxy, arylthio, substituted arylthio, aralkyl, substituted aralkyl, cycloalkyl, cycloalkalkyl, lower acyloxy, aryloxycarbonyl, lower alkoxycarbonyl, or lower haloalkenyloxy;

$R^{10}$ is hydrogen or lower alkyl; and $R^{11}$ is lower alkenyl, lower alkynyl, or aralkyl.

The compounds of the present invention represented by generic formula (A) are useful agents for the control of pests such as insects and acarids. Without any intention of being bound by theory and although the mode of action of the compounds of formula (A) as applied to the control of insects and acarids is not completely understood, the compounds of formula (A) appear to be effective for the control of insects and acarids by reason of mechanisms of the nature of the insect control agents known as pyrethrins and synthetic pyrethroids.

In the description hereinafter and the appended claims, each of $R^1$ through $R^{11}$, W, and t is as defined hereinabove, unless otherwise specified.

The compounds of formula (A) can be synthesized by the general reaction of an aldehyde of formula I with the carbanion of a phosphonate of formula II to form an ester of formula III. The ester of formula III is hydrolyzed to the acid or acid salt, which is esterified using an alcohol $R^5$—OH or a halide $R^5$—X to obtain the esters of formula (A).

$$R^1-CH_2-\overset{H}{\underset{\|}{C}}=O \qquad \underset{PO}{\overset{PO}{\underset{\diagup}{\diagdown}}}\overset{O}{\underset{\|}{P}}-\underset{\underset{|}{R^4}}{CH}-\overset{O}{\underset{\|}{C}}-OR'$$

(I)                          (II)

$$R^1-CH=CH-\underset{\underset{|}{R^4}}{CH}-\overset{O}{\underset{\|}{C}}-OR'$$

(III)

In the above formulas, each of R and R' is lower alkyl. The carbanion of the phosphonate of formula II is generated by treatment with sodium hydride or the like in dimethylformamide, tetrahydrofuran, or the like. Compounds of formula (A) wherein $R^2$ is lower alkyl, lower alkenyl or cycloalkalkyl can be prepared by the above sequence of reactions starting with a ketone of formula I'.

$$R^1-\underset{\underset{|}{R^2}}{C}=O \quad (I')$$

The following terms, wherever used in the description herein and the appended claims, have the meaning defined below, unless otherwise specified hereinafter.

The term "lower alkyl" refers to an alkyl group, straight or branched, having a chain length of one to six carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to six carbon atoms. The term "lower alkylthio" refers to an alkylthio group, straight or branched, having a chain length of one to six carbon atoms.

The term "lower alkenyl" refers to an ethylenically unsaturated hydrocarbon group, straight or branched, having a chain length of two to six carbon atoms and one or two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms. The term "lower alkenyloxy" refers to an alkenyloxy group, straight or branched, of two to six carbon atoms. The term "lower haloalkenyloxy" refers to a lower alkenyloxy group substituted with one to three halogen atoms.

The term "lower alkynyl" refers to an alkynyl group, straight or branched, having a chain length of two to six carbon atoms and one or two acetylenic bonds. The term "lower haloalkynyl" refers to a lower alkynyl group having one to three halogen atoms. The term "lower alkynyloxy" refers to an alkynyloxy group, straight or branched, of three to six carbon atoms.

The term "cycloalkyl" refers to a cycloalkyl group of three to six cyclic carbon atoms. The term "cycloalkalkyl" refers to a cycloalkyl group wherein one hydrogen atom is replaced by a lower alkyl group, the total number of carbon atoms being from four to eight, such as cyclopropanemethyl, cyclobutaneethyl, cyclohexanemethyl, and the like.

The term "aryl" refers to the aryl group phenyl or naphthyl. The term "aralkyl" refers to a lower alkyl group in which a hydrogen atom of the alkyl group is substituted by an aryl group, the total number of carbon atoms being from seven to twelve, such as benzyl, phenethyl, and the like. The terms "substituted aryl" and "substituted aralkyl" refer to an aryl group and an aralkyl group, respectively, substituted at one, two or three of the ring carbon atoms with a group selected from lower alkyl, lower haloalkyl, lower alkoxy, lower alkenyl, lower haloalkenyl, lower alkenyloxy, halogen, nitro, cyano, or lower alkylthio.

The term "lower haloalkoxy" refers to a lower alkoxy group substituted with one to three halogen atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The compounds of the present invention of formula A are useful pest control agents, particularly for the control of insects and acarids. In the use of the compounds of formula A for combatting insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

As shown hereinafter, the compounds of the present invention are effective on many different insects and on acarids. The compounds are effective control agents for insects such as mosquitoes, flies, aphids, weevils and acarids such as the spider mite and ticks. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates and insect growth regulators, e.g. propoxur, carbaryl, naled, dichlorvos, methoprene, kinoprene, hydroprene, cyhexatin, resmethrin, and permethrin.

The following examples are provided to illustrate the practice of the present invention. Temperature is given in degrees Centigrade. RT means room temperature.

EXAMPLE 1

A. Sodium hydride (1.70 g., 57% in oil dispersion) is washed free of oil using hexane under nitrogen, and then 7.4 g (20 mmole) of triphenylphosphine hydroxycarbonylethylene and 2.4 g (20 mmole) of acetophenone in 25 ml of dimethylsulfoxide (DMSO) and 20 ml of tetrahydrofuran (THF) are added. The reaction is stirred overnight at RT and then poured into ether and water. The aqueous phase is washed (2X) with ether and then acidified with 2 N sulfuric acid followed by extraction into ether. The organic phase is washed with water, dried over calcium sulfate and solvent removed to give 4-phenyl-3-pentenoic acid.

B. To 3.2 ml (23 mmole) diisopropylamine in 15 ml THF at 0° under nitrogen is added 14.4 ml (23 mmole) 1.6 M n-butyllithium. The reaction is warmed to RT over 2 hr and cooled to 0°, and 2.0 g (11.4 mmole) 4-phenyl-3-pentenoic acid in several ml of THF is added. After 1.5 hr at about 10°, 1.16 ml (11.6 mmole) isopropyl iodide is added and the reaction stirred about 60 hours. The reaction is poured into water and hexane. The aqueous phase is acidified and extracted with ether. The ether extracts are washed to neutrality, dried over calcium sulfate and solvent removed under vacuum to give 2-isopropyl-4-phenyl-3-pentenoic acid.

C. To 2.14 g (10 mmole) of the thus-obtained acid, 10 ml ether and 10 ml hexamethylphosphorictriamide (HMPT), under nitrogen, is added 1.45 g (10.5 mmole) potassium carbonate and 2.76 g (10.5 mmole) m-phenoxybenzyl bromide. The reaction is stirred about 16 hr and then poured into hexane and water. The organic phase is washed with water, saturated sodium chloride, and dried over calcium sulfate. Solvent is removed by rotoevaporation to yield the m-phenoxybenzyl ester of 2-isopropyl-4-phenyl-3-pentenoic acid, which can be further purified by preparatory thin layer chromatography (prep. TLC) eluting with 2.5% ethyl acetate/hexane, MS m/e 400 (M+, 15), 183 (100).

EXAMPLE 2

To 12 g of 3-benzoylpropionic acid and 9.3 g of potassium carbonate in 100 ml of dimethylformamide (DMF), under nitrogen, is added m-phenoxybenzyl bromide (17.1 g). The reaction is stirred about 4 hr and then water added followed by extraction with ether. The combined extracts are washed with water, saturated sodium chloride, dried over calcium sulfate and rotoevaporated to give m-phenoxybenzyl 3-benzoylpropionate which can be further purified by prep. TLC eluting with 15% ethyl acetate/hexane.

To a refluxing mixture of phosphorus pentachloride (5.8 g) and carbon tetrachloride (25 ml) is slowly added m-phenoxybenzyl 3-benzoylpropionate (5 g) in carbon tetrachloride (10 ml) over about 45 minutes. Refluxing is continued about 0.5 hr and then the reaction is poured onto ice and extracted with ether. The ether extracts are combined, washed with saturated sodium bicarbonate, water and saturated sodium chloride, dried over calcium sulfate and solvent evaporated. The product is subjected to prep. TLC using 12% ethyl acetate/hexane and the major band collected to yield m-phenoxybenzyl 4-chloro-4-phenyl-3-butenoate.

Following Example 1B, the anion of the above ester is prepared at −78°, isopropyl iodide is added and the reaction, after warming to RT, is allowed to stand 3 hr to give m-phenoxybenzyl ester of 2-isopropyl-4-chloro-4-phenyl-3-butenoic acid, MS m/e 420 (M+).

EXAMPLE 3

Sodium hydride (0.29 g, 57% oil dispersion) is washed with pentane and then 25 ml DMF is added and cooled to 0°. Diethyl ethoxycarbonylisobutylenephosphonate (1.67 g) is added and stirred. Then 4-methoxyphenylethanal (0.95 g) is added. The reaction is stirred for about 20 hr and then added to hexane/water. The aqueous phase is extracted with ether and combined with the organic phase which is washed with brine, dried over sodium sulfate and solvent evaporated. The crude product is subjected to prep. TLC using 7.5% ethyl acetate/hexane and then 4% ethyl acetate/hexane to give ethyl 2-isoproyl-4-(4-methoxyphenyl)-3-butenoate.

The thus-prepared ester is hydrolyzed by treatment with potassium hydroxide in methanol/water to give 2-isopropyl-4-(4-methoxyphenyl)-3-butenoic acid, which is reacted with m-phenoxybenzyl bromide using the procedure of Example 1 to give m-phenoxybenzyl 2-isopropyl-4-(4-methoxyphenyl)-3-butenoate, MS m/e 416 (M+).

The process of Example 3 is repeated starting with 4-methylphenylethanal to prepare ethyl 2-isopropyl-4-(4-methylphenyl)-3-butenoate and 2-isopropyl-4-(4-methylphenyl)-3-butenoic acid, respectively, and as the final product, m-phenoxybenzyl 2-isopropyl-4-(4-methylphenyl)-3-butenoate.

NMR (CDCl$_3$) δ 0.89 [d, 3, J=7 Hz, —CH(CH$_3$)$_2$], 0.92 [d, 3, J=7 Hz, —CH(C$\underline{H}_3$)$_2$], 2.33 (s, 3,

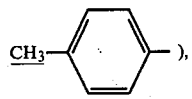), 5.14 (s, 2,

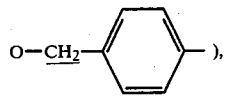), and 5.7–6.7 ppm (complex, 2, vinyl). IR (CCl$_4$) 1743 cm$^{-1}$ (C=O).

EXAMPLE 4

Following the procedure of Example 3, phenylacetaldehyde is converted into ethyl 2-isopropyl-4-phenyl-3-butenoate, which is hydrolyzed using potassium hydroxide to 2-isopropyl-4-phenyl-3-butenoic acid. To the acid (0.31 g) in 5 ml ether and 3 drops DMF, cooled to 0° under nitrogen, is added thionyl chloride (0.29 g) while stirring. After about 30 min at RT, the reaction is refluxed for about 45 min, then cooled to RT and concentrated by rotoevaporation under vacuum. To the concentrate is added 5 ml ether, 0.25 ml pyridine and 0.38 g m-phenoxybenzyl cyanohydrin in ether. The reaction mixture is stirred about 20 hr at RT and then poured into 5% sodium hydroxide-ether, which is extracted with ether. The ether layers are combined, washed with 2 N hydrochloric acid, sodium bicarbonate, water and brine, dried over sodium sulfate and solvent removed by rotoevaporation in vacuum. The product is subjected to prep. TLC eluting with 20% ether/hexane to give m-phenoxy-α-cyanobenzyl 2-isopropyl-4-phenyl-3-butenoate, MS m/e 711 (M+).

Following the procedure of Example 3, m-chlorophenylacetaldehyde is converted into ethyl 2-isopropyl-4-(m-chlorophenyl)-3-butenoate which is hydrolyzed using potassium hydroxide to the acid, 2-isopropyl-4-(m-chlorophenyl)-3-butenoic acid, which is reacted with m-phenoxybenzyl bromide to yield the m-phenoxybenzyl ester of 2-isopropyl-4-(m-chlorophenyl)-3-butenoic acid, MS m/e 420 (M+).

EXAMPLE 5

Sodium hydride (5.26 g, 57% in oil) is washed with dry pentane under nitrogen and 50 ml DMF added followed by 24 ml (0.120 moles) diethylethoxycarbonylmethylenephosphonate. The reaction is stirred 1 hr at 0°–10° and 14 ml (0.114 mole) phenylacetaldehyde is added slowly. The reaction is stirred about 20 hrs and then poured into water-hexane. The aqueous phase is extracted with hexane. The organic phases are combined, washed with water and sat. sodium chloride, dried over calcium sulfate and rotoevaporated to give ethyl 4-phenyl-3butenoate.

To sodium hydride (2.84 g, 57% in oil, washed with pentane), 110 ml dry THF and 20 ml HMPT, cooled to 0° and under nitrogen, is added 12.7 g ethyl 4-phenyl-3-butenoate slowly with stirring. Then 6.5 ml of isopropyliodide is added and the reaction mixture is stirred for about 60 hrs. The reaction is worked up by extracting into water/ether mixture. The aqueous phase is extracted with ether. The organic phases are combined, washed with brine, dried over calcium sulfate and rotoevaporated to give ethyl 2-isopropyl-4-phenyl-3-butenoate, which is hydrolyzed (potassium hydroxide, water-methanol) to the acid, 2-isopropyl-4-phenyl-3-butenoic acid. The acid is reacted with m-phenoxybenzyl alcohol following the procedure of Example 4 to yield m-phenoxybenzyl ester of 2-isopropyl-4-phenyl-3-butenoic acid.

NMR (CDCl$_3$) δ 0.91 [d, 3, J=Hz, —CH(CH$_3$)$_2$], 0.94 [d, 3, J=Hz, —CH(C$\underline{H}_3$)$_2$], 5.13 (s, 2, benzyl), and 6.0–6.5 ppm (complex, 2, vinyl). IR (CCl$_4$) 1745 cm$^{-1}$ (C=O).

The process of Example 3 is repeated using p-chlorophenyl acetaldehyde in place of phenylacetaldehyde to give ethyl 2-isopropyl-4-(p-chlorophenyl)-3-butenoate, which is hydrolyzed to the acid, 2-isopropyl-4-(p-chlorophenyl)-3-butenoic acid, a yellow solid. The acid is reacted with m-phenoxybenzyl bromide according to the procedure of Example 1 to yield the m-phenoxybenzyl ester of 2-isopropyl-4-(p-chlorophenyl)-3-butenoic acid, MS m/e 420 (M+).

EXAMPLE 6

To zinc dust (1.17 g, 18 mmole), in a round bottom flask with reflux condenser, under nitrogen, is added several ml of ether, methyl benzyl ketkone (2.01 g, 15 mmol) in ether, ethyl bromoacetate (2.84 g, 17 mmole), 10 ml ether and 20 ml benzene. The reaction mixture is. heated, iodide crystal added, and heating continued to reflux with stirring for about 1 hour. The reaction is checked by TLC and then a small amount of cold 10% sulfuric acid is added and stirred for 1 hour. The organic layer is washed with 10% sulfuric acid (2X), 2 M sodium carbonate, and water (2X), dried over calcium sulfate and rotoevaporated to yield ethyl 3-hydroxy-3-methyl-4-phenylbutanoate.

To mixture of the above hydroxy-ester (3.06 g, 13.76 mmole) and pyridine (10 ml), cooled to 0° C., is slowly added phosphorus oxychloride (3.59 g, 23.39 mmole). The reaction mixture is stirred for about 2 hrs and then heated to 100° for 1.5 hours. The reaction is worked up by pouring into ice and extracting with water-hexane. The aqueous layer is back-extracted with hexane. The organic phases are combined, washed with 2 N hydrochloric acid, water and brine, dried over sodium sulfate and rotoevaporated to yield a mixture of esters—ethyl 3-methyl-4-phenyl-3- butenoate and ethyl 3-methyl-4-phenyl-2-butenoate. The mixture of esters is hydrolyzed using potassium hydroxide, water/methanol at 40° for about 20 hrs to yield the acids, 3-methyl-4-phenyl-3-butenoic acid and some 3-methyl-4-phenyl-2-butenoic acid.

To a mixture of diisopropyl amine (1.92 g, 19 mmole) and 27 ml THF, cooled, is added n-butyllithium (19 mmole) over 1 hour. The mixture is stirred at RT for 2 hrs and then the above prepared acids (1.59 g, 9.02 mmole) added. The reaction is stirred at RT for 3 hrs and then 10 ml HMPT and 1.53 g isopropyl iodide added. Stirring is continued for about 20 hrs and then the mixture is worked up by pouring into dilute aqueous sodium hydroxide and extracting with ether. The aqueous layer is acidified with 2 N sulfuric acid and extracted with ether. The organic phases are combined, washed with water and brine, dried over sodium sulfate and rotoevaporated to yield 2-isopropyl-3-methyl-4-phenyl-3-butenoic acid and some α,β-unsaturated acid.

The thus-prepared acid (6.92 mmole) is esterified using m-phenoxybenzyl bromide (2.26 g), potassium carbonate (1.19 g) and HMPT and the prduct is purified by prep TLC eluting with 4% ethyl acetate/hexane (band 1) to give m-phenoxybenzyl 2-isopropyl-3-methyl-4-phenyl-3-butenoate (67.6% trans, 32.4% cis), MS m/e 400 (M+).

EXAMPLE 7

The process of Example 3 is repeated using o-chlorophenylacetaldehyde to prepare ethyl 2-isopropyl-4-(o-chlorophenyl)-3-butenoate, which is hydrolyzed (potassium hydroxide-water/methanol) to the acid, 2-isopropyl-4-(o-chlorophenyl)-3-butenoic acid. The acid is reacted with m-phenoxybenzyl bromide as in Example 1 to yield m-phenoxybenzyl 2-isopropyl-4-(o-chlorophenyl)-3-butenoate. MS m/e 420 (M+).

EXAMPLE 8

Each of the acids,
2-isopropyl-4-phenyl-3-pentenoic acid,
2-isopropyl-4-(4-methoxyphenyl)-3-butenoic acid,
2-isopropyl-4-(4-methylphenyl)-3-butenoic acid,
2-isopropyl-4-(4-chlorophenyl)-3-butenoic acid,
2-isopropyl-3-methyl-4-phenyl-3-butenoic acid, and
2-isopropyl-4-(2-chlorophenyl)-3-butenoic acid
is reacted with m-phenoxybenzyl cyanohydrin using the process of Example 4 to prepare the respective m-phenoxy-α-cyanobenzyl ester of each acid.

EXAMPLE 9

To p-fluorophenethyl alcohol (4.5 g, 31.9 mmol) in 50 ml dichloromethane is added sodium acetate (0.5 g, 6.2 mmol) and pyridinium chlorochromate (10.4 g, 48.1 mmol) with stirring, at RT and under nitrogen. The reaction mixture is stirred for about 2 hours and then filtered through a column of Florisil using dichloromethane. The filtrate is dried, concentrated under vacuum and distilled (short path) to yield p-fluorophenylacetaldehyde (fraction at 90°, 3.5 mm Hq.).

Sodium hydride, 57% oil dispersion (8.31 mmol) is washed with pentane and then 10 ml DMF is added and cooled to about 0°. Then diethyl ethoxycarbonylisobutylenephosphonate (2.3 g, 8.6 mmol) is added, the mixture stirred for about 45 minutes, followed by p-fluorophenylacetaldehyde (1.2 g, 8.4 mmol). The reaction mixture, under nitrogen, is stirred for about 36 hours (followed by TLC) and then added to ether/water. The ether phase is washed with water and brine, dried over sodium sulfate and solvent evaporated. The crude product is plated on silica gel plates eluting with 7.5% ether-hexane to obtain ethyl 2-isopropyl-4-(4-fluorophenyl)-3-butanoate.

A mixture of the above ester (0.46 g), potassium hydroxide (2.5 mmol), 3 ml methanol and 0.5 ml water is stirred at about 45° overnight. Methanol is removed by evaporation and then 5% NaOH-ether is added. After adjusting to about pH 3 by addition of dilute HCl, the mixture is extracted with ether. The ether phase is washed with water and brine, dried over sodium sulfate, and solvent evaporated to yield 2-isopropyl-4-(4-fluorophenyl)-3-butenoic acid.

A mixture of the above acid (0.32 g), 3 m of ether, thionyl chloride (0.21 ml) and a few drops of DMF is stirred, under nitrogen, at RT for 1.5 hour and then heated at reflux for 1 hour. After cooling, the reaction mixture is concentrated under vacuum. To the concentrate is added 5 ml ether, cooled to about 5°, followed by 0.15 ml pyridine and m-phenoxybenzyl alcohol (0.33 g, 1.81 mmol). The reaction mixture is stirred overnight at RT and then water/ether is added. The ether phase is washed with dilute HCl, water and brine, dried over sodium sulfate and solvent removed under vacuum. The crude product is plated on silica gel plates eluting with 7.5% ether/hexane to yield m-phenoxybenzyl 2-isopropyl-4-(4-fluorophenyl)-3-butenoate, MS m/e 404.4 (M+).

2-Isopropyl-4-(4-fluorophenyl)-3-butenoic acid (1.12 mmol) is reacted via the acid chloride with α-cyano-m-phenoxybenzyl alcohol (1.86 mmol) to yield α-cyano-m-phenoxybenzyl 2-isopropyl-4-(4-fluorophenyl)-3-butenoate, MS m/e 429 (M+).

EXAMPLE 10

Following the procedures herein (e.g. Examples 4 and 9), each of 4-trifluoromethylphenylacetaldehyde, 2-trifluorometnylphenylacetaldehyde, 2,4-difluorophenylacetaldehyde, pentafluorophenylacetaldehyde, and 2-fluoro-4-trifluoromethylphenylacetaldehyde is reacted with the carbanion of diethoxyethoxycarbonylisobutylenephosphonate to yield the respective acid under column I, which is esterified via the acid chloride by reaction with m-phenoxybenzyl alcohol to yield the respective ester under column II.

I 2-isopropyl-4-(4-trifluoromethylphenyl)-3-butenoic acid
2-isopropyl-4-(2-trifluoromethylphenyl)-3-butenoic acid
4-(2,4-difluorophenyl)-2-isopropyl-3-butenoic acid
2-isopropyl-4-pentafluorophenyl-3-butenoic acid
4-(2-fluoro-4-trifluoromethylphenyl)-2-isopropyl-3-butenoic acid

II m-phenoxybenzyl 2-isopropyl-4-(4-trifluoromethylphenyl)-3-butenoate
m-phenoxybenzyl 2-isopropyl-4-(2-trifluoromethylphenyl)-3-butenoate
m-phenoxybenzyl 4-(2,4-difluorophenyl)-2-isopropyl-3-butenoate
m-phenoxybenzyl 2-isopropyl-4-pentafluorophenyl-3 butenoate
m-phenoxybenzyl 4-(2-fluoro-4-trifluoromethylphenyl)-2-isopropyl-3-butenoate

EXAMPLE 11

To a mixture of 2-isopropyl-4-phenyl-3-butenoic acid (0.22 g, 1.07 mmol), 2 ml DMF, 3 ml THF and potassium carbonate (0.23 g, 1.66 mmol) is added m-phenylcarbonylbenzyl bromide (0.33 g, 1.2 mmol). The reaction mixture is stirred overnight at RT and then ether/water is added. The ether phase is washed with 5% NaOH, water and brine, dried over sodium sulfate and concentrated under vacuum. The crude product is plated on silica gel plates eluting with 10% ether/hexane to yield m-phenylcarbonylbenzyl 2-isopropyl-4-phenyl-3-butenoate, MS m/e 398.3 (M+).

EXAMPLE 12

Following the procedure of Example 9, each of 2-naphthylacetaldehyde and 2-fluoro-4-methylphenylacetaldehyde is reacted with the carbanion of diethoxy ethoxycarbonylisobutylenephosphonate to yield 2-isopropyl-4-(2-naphthyl)-3-butenoic acid and 4-(2-fluoro-4-methyl)-2-isopropyl-3-butenoic acid. Each acid, via the acid chloride, is reacted with α-cyano-m-phenoxybenzyl alcohol to prepare the ester—that is, α-cyano-m-phenoxybenzyl 2-isopropyl-4-(2-naphthyl)-3butanoate and α-cyano-m-phenoxybenzyl 4-(2-fluoro-4-methylphenyl)-3-butenoate.

In the same way, α-cyano-m-phenoxybenzyl 2-isopropyl-4-(1-naphthyl)-3-butanoate is prepared from the acid chloride of 2-isopropyl-4-(1-naphthyl)-3-butenoic acid. The acid is prepared as above from 1-naphthylacetaldehyde.

EXAMPLE 13

2-Fluorophenylacetaldehyde is converted into ethyl 4-(2-fluorophenyl)-4-isopropyl-3-butanoate and hydrolyzed to the acid using the procedure of Example 9. The acid, 4-(2-fluorophenyl)-2-isopropyl-3-butenoic acid, is reacted, via the acid chloride, with m-phenoxybenzyl alcohol to yield m-phenoxybenzyl 4-(2-fluorophenyl)-2-isopropyl-3-butenoate, MS m/e 404.3 (M+). 2-Fluorophenylacetaldehyde is prepared from o-fluoro-β-methoxystyrene via the dimethylacetal using the procedure of Winterfeldt, *Berichte* 96(12), 3349 (1963).

EXAMPLE 14

3-Fluorophenylacetaldehyde is converted into ethyl 4-(3-fluorophenyl)-2-isopropyl-3-butenoate using the reaction of Example 9. The ester is hydrolyzed using KOH/MeOH/H$_2$O to 4-(3-fluorophenyl)-2-isopropyl-3-butenoic acid, which is converted to the acid chloride and reacted with α-cyano-m-phenoxybenzyl alcohol to yield α-cyano-m-phenoxybenzyl 4-(3-fluorophenyl)-2-isopropyl-3-butenoate, MS m/e 429 (M+).

The acid chloride of 4-(3-fluorophenyl)-2-isopropyl-3-butenoic acid is reacted with m-phenoxybenzyl alcohol to yield m-phenoxybenzyl 4-(3-fluorophenyl)-2-isopropyl-3-butenoate, MS m/e 404 (M+).

EXAMPLE 15

To a polyethylene flask containing 16 ml of 70% HF in pyridine (Aldrich Chemical Company) and 10 ml of sulfolane is added 1.78 g (10 mmol) of N-bromosuccinimide and then 1.18 g (10 mmol) of β-methylstyrene. After several hours, the mixture is poured onto ice and the halogenated intermediate extracted into ether. The organic phase is washed with sat. NaCl solution and dried (Na$_2$SO$_4$) and solvent removed under vacuum.

The oily residue is treated with several equivalents of potassium t-butoxide in t-butanol. After about 6 hours, the reaction mixture is poured into water and pentane. The pentane layer is separated, washed with sat. NaCl solution, dried (Na$_2$SO$_4$) and solvent removed under vacuum to yield α-fluoro-β-methylstyrene.

To 1.36 g (10 mmol) of α-fluoro-β-methystyrene in 20 ml of CCl$_4$ is added 1.78 g (10 mmol) of N-bromosuccinimide and 50 mg of dibenzoyl peroxide. The reaction is stirred overnight and then poured into hexane and water. The hexane layer is shaken against sat. NaCl solution and dried (Na$_2$SO$_4$). The product bromide after solvent removal is dissolved in 10 ml of THF and 10 ml of HMPT, and 1.96 g (40 mmol) of sodium cyanide is added. The reaction is warmed to 60° and after 24 hours poured into ether/hexane (2:8) and water. The organic phase is washed several times with water, dried, and solvent removed to give 4-fluoro-4-phenyl-3-butanonitrile.

To 240 mg (10 mmol) of sodium hydride (washed free of oil with pentane) in THF under nitrogen is added 1.61 g (10 mmol) of 4-fluoro-4-phenyl-3-butenonitrile followed by 1.70 g (10 mmol) of isopropyl iodide. The reaction is warmed to 50° overnight, and then the reaction mixture is poured into ether and water. The organic phase is washed with sat. NaCl solution and dried (Na$_2$SO$_4$).

After removal of solvent, the cyanide is hydrolyzed to the corresponding acid by heating it in 50% H$_2$SO$_4$ (aqueous) for about 8 hours. The reaction mixture is poured into water and ether. The organic phase is washed once with sat. NaCl solution, dried (Na$_2$SO$_4$) and solvent removed to give 4-fluoro-2-isopropyl-4-phenyl-3-butenoic acid.

Following the procedure of Example 1C, the acid is converted to m-phenoxybenzyl 4-fluoro-2-isopropyl-4-phenyl-3-butenoate.

Following the procedure of Example 4, the acid is converted to m-phenoxy-α-cyanobenzyl 4-fluoro-2-isopropyl-4-phenyl-3-butenoate.

EXAMPLE 16

To a suspension of sodium hydride (0.64 g, 15.2 mmol), washed with pentane, in 30 ml of THF at 0° and under nitrogen, is slowly added α-fluoro-triethylphosphonacetate (3.68 g, 15.2 mmol). After stirring about 0.5 hour, benzaldehyde (1.6 g, 15.1 mmol) in THF, at 0°, is added. The reaction mixture is allowed to rise to RT overnight. Reaction is worked up by extracting in ether/water. Aqueous layer is back-extracted with ether. The ether layers are combined, washed with water and brine, dried over sodium sulfate, and evaporated. The product is plated on silica gel prep. TLC plates eluting with ether/hexane to yield ethyl 2-fluoro-3-phenyl-2-propenoate.

To a solution of the above ester (1.80 g, 9.27 mmol) in 50 ml benzene is added dripwise at RT a 1.78 M solution of diisobutyl aluminum hydride; stir 20 minutes. Add 3 ml more diisobutyl aluminum hydride. Reaction is worked up by adding MeOH until hydrogen evolution ceases, then extracting in ether/dilute HCl solution. The aqueous layer is extracted 2X with ether. The ether layers are washed with dil. HCl, water and brine, dried (Na$_2$SO$_4$) and evaporated under vacuum to yield 2-fluoro-3-phenyl-2-propen-1-ol.

To the above alcohol (1.27 g, 8.34 mmol) in 50 ml ether at 0° under nitrogen is added phosphorus tribromide (2.25 g, 8.31 mmol). The reaction mixture is stirred about 2 hours as followed by TLC. The reaction mixture is worked up by pouring onto ice, then extracting with ether/water. The aqueous layer is extracted with ether. The combined ether phases are washed with water and brine, dried (Na$_2$SO$_4$) and evaporated to yield 2-fluoro-3-phenyl-2-propen-1-yl bromide.

To the above bromide (1.52 g, 7.07 mmol) in 15 ml of THF and 10 ml of HMPT is added NaCN (1.4 g, 28.56 mmol). The reaction mixture is heated to 60° for about 24 hours. After cooling, the reaction is worked up in ether/water. The aqueous layer is extracted with ether. The combined ether phases are washed with water and brine, dried (Na$_2$SO$_4$) and evaporated to yield 2-fluoro-3-phenyl-2-propen-1-yl nitrile.

A suspension of washed sodium hydride (0.265 g, 6.29 mmol) in 20 ml THF and 3 ml HMPT and the above nitrile (1.01 g, 6.26 mmol), under nitrogen, is stirred about 30 minutes. Isopropyl iodide (6.3 mmol) is added and the mixture heated to 50° overnight. After cooling, the reaction mixture is extracted in ether/water. Aqueous layer is extracted with ether and the combined ether phases are washed with water and brine, dried (Na$_2$SO$_4$) and evaporated to yield 2-fluoro-1-isopropyl-3-phenyl-2-propenyl nitrile.

A mixture of the above nitrile (0.82 g, 4.03 mmol) and 10 ml 50% H$_2$SO$_4$ is heated for about 15 hours at 60°. After cooling, the reaction is worked up by extracting in ether/dil. H$_2$SO$_4$ solution. The aqueous layer is extracted a total of three times with ether. The combined ether phases are extracted 2X with 5% NaOH solution. The basic aqueous phases are acidified with HCl and then extracted 3X with ether. The combined ether phases are washed with water and brine, dried (Na$_2$SO$_4$) and evaporated to yield 3-fluoro-2-isopropyl-4-phenyl-3-butenoic acid.

The above acid is reacted with m-phenoxybenzyl cyanohydrin following the procedure of Example 4 to yield m-phenoxy-α-cyanobenzyl 3-fluoro-2-isopropyl-4-phenyl-3-butenoate.

Similarly, following the procedure of Example 1, the acid is reacted with m-phenoxybenzyl bromide to yield m-phenoxybenzyl 3-fluoro-4-phenyl-3-butenoate.

Yound lima bean leaves (in water) infested with approximately 50 adult *Tetranychus urticae* are sprayed to runoff with test compound 2 [α-cyano-m-phenoxybenzyl 4-(4-fluorophenyl)-2-isopropyl-3-butenoate] diluted to three different concentrations in aqueous carrier containing 0.025% Tween 20 and 0.1% wetting agent. The treated leaves are maintained at 24° and 16 hr photoperiod for 2 days. Live adult mites are then counted and subtracted from the original total to obtain the number affected, which is started as a percentage of the total. Correction is made for any control mortality using Abbott's formula. The compound had an LC$_{50}$ of less than 10 ppm (parts per million).

Fifteen 72-hour-old adult female *Musca domestica* L. are anesthetized with ether vapor. These are then treated with 1 ul of test compound 2 diluted to three different concentrations in acetone applied to the dorsal surface of the prothorax. They are held in an assay container with milk-saturated cotton at 25°, 16 hr photoperiod for 24 hours. The effect is stated as the number dead calculated as a percentage of the total, corrected for any control mortality using Abbott's formula. The compound gave an LC$_{50}$ of less than 0.01%.

Two groups of 10 each of 0–24 hour II instar *Heliothis virescens* larvae are treated with 1 ul of test compound 2 in acetone at three different concentrations by application to the dorsum of the thorax. Two groups of 10 each are treated identically with 1 ul acetone as controls. Larvae are held individually in 30 ml plastic cups provided with artificial medium for 72 hours at 25° and 16 hr photoperiod. After 72 hours the number of dead is calculated as a percentage of the total number originally treated and then corrected for any mortality in the control groups using Abbott's formula. The LC$_{50}$ of the compound was less than 0.01%.

What is claimed is:

1. A compound of the following formula:

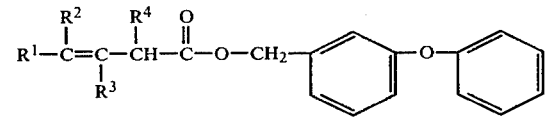

wherein,
R$^1$ is naphthyl, phenyl or substituted phenyl in which the phenyl group is substituted at one, two or three of the ring carbon atoms with lower alkyl, lower haloalkyl, lower alkoxy or halogen;
each of R$^2$ and R$^3$ is independently selected from hydrogen, chloro, fluoro or methyl; and
R$^4$ is lower alkyl of 2 to 5 carbon atoms.

2. A compound according to claim 1 wherein R$^4$ is isopropyl.

3. A compound according to claim 2 wherein R$^1$ is phenyl or substituted phenyl.

4. A compound according to claim 2 wherein R$^1$ is substituted phenyl.

5. A compound according to claim 4 wherein R$^1$ is a para-substituted phenyl, ortho-substituted phenyl, or ortho, para-disubstituted phenyl.

6. A compound according to claim 5 wherein R$^2$ is fluoro or hydrogen, and R$^3$ is hydrogen.

7. A compound according to claim 5 wherein R$^2$ is hydrogen and R$^3$ is fluoro or hydrogen.

8. The compound, m-phenoxybenzyl 4-(4-fluorophenyl)-2-isopropyl-3-butenoate, according to claim 5.

9. The compound, m-phenoxybenzyl 2-isopropyl-4-phenyl-3-pentenoate, according to claim 2.

10. The compound, m-phenoxybenzyl 4-chloro-2-isopropyl-4-phenyl-3-butenoate, according to claim 2.

11. The compound, m-phenoxybenzyl 4-(4-chlorophenyl)-2-isopropyl-3-butenoate, according to claim 2.

12. The compound, m-phenoxybenzyl 2-isopropyl-4-phenyl-3-butenoate, according to claim 2.

13. The compound, m-phenoxybenzyl 2-isopropyl-4-(4-trifluoromethylphenyl)-3-butenoate, according to claim 2.

14. The compound, m-phenoxybenzyl 4-(2-fluoro-4-trifluoromethylphenyl)-3-butenoate, according to claim 2.

15. The compound, m-phenoxybenzyl 2-isopropyl-4-pentafluorophenyl-3-butenoate.

* * * * *